United States Patent [19]

Thyrum

[11] Patent Number: 4,895,843

[45] Date of Patent: Jan. 23, 1990

[54] USE OF 3-(4-BROMO-2-FLUOROBENZYL)-4-OXO-3H-PHTHALAZIN-1-YLACETIC ACID AS A HYPOURICAEMIC AGENT

[75] Inventor: Per T. Thyrum, Wilmington, Del.

[73] Assignee: ICI Americas, Inc., Wilmington, Del.

[21] Appl. No.: 154,019

[22] Filed: Feb. 9, 1988

[30] Foreign Application Priority Data

Feb. 26, 1987 [GB] United Kingdom ............... 8704569

[51] Int. Cl.$^4$ .................... C07D 237/32; A61K 31/50
[52] U.S. Cl. .................................................. 514/248
[58] Field of Search .................. 544/237; 514/248

[56] References Cited

U.S. PATENT DOCUMENTS 4,251,528 2/1981 Brittain .................. 544/237
4,393,062 7/1983 Brittain .................. 544/237

FOREIGN PATENT DOCUMENTS 0002895 7/1979 European Pat. Off. .

Primary Examiner—Mark L. Berch
Attorney, Agent, or Firm—Cushman, Darby & Cushman

[57] ABSTRACT

The invention concerns a novel therapeutic agent for use in reducing raised serum uric acid levels comprising 3-(4-bromo-2-fluorobenzyl)-4-oxo-3H-phthalazin-1-ylacetic acid or a pharmaceutically acceptable salt thereof.

3 Claims, No Drawings

USE OF 3-(4-BROMO-2-FLUOROBENZYL)-4-OXO-3H-PHTHALAZIN-1-YLACETIC ACID AS A HYPOURICAEMIC AGENT

This invention concerns a novel therapeutic agent and, more particularly, a novel therapeutic agent for use in lowering blood uric acid levels in man, that is a novel hypouricaemic agent. The invention also concerns the use of the therapeutic agent in the production of a novel medicament for reducing blood uric acid levels and a method of medical treatment or prophylaxis which involves reducing blood uric acid levels by administration of said therapeutic agent to man. Uric acid is the principal product of the metabolism in man of purine derivatives such as nucleic acids.

The normal plasma concentration of uric acid is close to the solubility limit, beyond which crystal deposition tends to occur in various tissues throughout the body, leading to the disease condition known as gout and gouty arthritis. The uric acid containing deposits (also known as tophi) in such conditions may occur in cartilage, bone, bursae, tendons, connective tissue overlying bony prominences, as well as sub-cutaneously and in the area of the kidney. Elevated blood uric acid levels (hyperuricaemia) may be caused by dietary absorption of uric acid or purine derivatives and also occur in a number of disease conditions. The latter include, for example, pneumonia, blood diseases involving a large turnover of purine nucleotides (such as myeloid leukaemia, myeloid dysplasia and pernicious anaemia), psoriasis, diabetes mellitus and renal disease. In addition, hyperuricaemia may also occur following the cytotoxic chemotherapy or radiotherapy of neoplasms, after the administration of pyrazinamide or of various hypotensive agents affecting renal function, or as a result of excessive biosynthesis arising from a genetic defect.

A number of therapeutic agents are known which lower blood uric acid levels (that is which possess a hypouricaemic effect). Such agents include, for example, probenecid, sulphinpyrazone and allopurinol and operate by various different mechanisms such as inhibiting uric acid formation (allopurinol) and increasing renal excretion (probenecid). However, there is a continuing need for new therapeutic agents which exert a hypouricaemic effect.

We have now surprisingly discovered that the known therapeutic agent ponalrestat (trade mark 'Statil', the property of Imperial Chemical Industries PLC: chemical name 3-(4-bromo-2-fluorobenzyl)-4-oxo-3H-phthalazin-1-ylacetic acid) shows significant, therapeutically valuable hypouricaemic effects in man. This agent has previously been described in European patent, publication number 2895B1, as an in vivo inhibitor of the enzyme aldose reductase, of value in the treatment of certain peripheral side-effects of diabetes mellitus and galactosemia such as diabetic cataract, retinopathy, neuropathy and renal papillary necrosis. The agent has also been described in the same European patent as having anti-inflammatory/analgesic properties. However, there was hitherto no suggestion that the agent might have hypouricaemic properties.

According to the invention there is provided a novel therapeutic agent for use in lowering blood uric acid levels (that is a hypouricaemic agent) which comprises 3-(4-bromo-2-fluorobenzyl)-4-oxo-3H-phthalazin-1-ylacetic acid of the formula I, or a pharmaceutically acceptable salt thereof.

The invention further provides the use of said compound of formula I, or of a pharmaceutically acceptable salt thereof, in the manufacture of a novel medicament for the production of a hypouricaemic effect.

The invention still further includes a method for the production of a hypouricaemic effect in a warm blood animal (including a human being) requiring such treatment which comprises administering to said animal a hypouricaemically effective amount of said compound of formula I, or of a pharmaceutically acceptable salt thereof.

Suitable pharmaceutically acceptable salts of the compound of formula I include, for example those described in European patent, publication number 2895B1, for example, alkali metal and alkaline earth metal salts (such as sodium, potassium, calcium or magnesium salts), aluminium and ammonium salts, and salts with organic bases affording a pharmaceutically acceptable cation such as salts with triethanolamine. A preferred salt of the compound of formula I for use as a hypouricaemic agent is, for example a potassium or sodium salt.

The compound of formula I may be obtained by one of the procedures described in European Patent, publication number 2895B1, for example that described in Example 4 of said publication. The compound has previously been referred to as 2-(2-fluoro-4-bromobenzyl)-1,2-dihydro-1-oxophthalazin-4-ylacetic acid, but the name given hereinabove is now preferred.

In use, the compound of the formula I will generally be administered for its hypouricaemic effects in the form of a conventional pharmaceutical composition, for example, such as is described in European patent, publication number 2895B1, and generally in a form suitable for oral administration (e.g. as a tablet, capsule, suspension or solution).

In general, the therapeutic agent will be administered at a daily dose in the range, for example 0.5 to 30 mg/kg orally so that typically a total daily dose in the range, for example, 25 to 600 mg (such as in the range 50–400 mg) of active ingredient per human is received. However, it will be readily understood that it may be necessary to vary the dose of therapeutic agent administered in accordance with well known medical practice to take account of the nature and severity of the hyperuricaemia under treatment and the age, weight and sex of the patient receiving the treatment.

In general, the compound of formula I and its pharmaceutically acceptable salts thereof begin to show significant and useful hypouricaemic effects at doses (for example about 50 mg per patient) which are below those required to produce in vivo inhibition of the enzyme aldose reductase and significantly below those required to produce anti-inflammatory/analgesic effects.

The invention will now be illustrated by the following non-limiting Examples: [Note: references to ponalrestat hereinbelow are to the compound of formula I referred to hereinabove i.e. to 3-(4-bromo-2-fluorobenzyl)-4-oxo-3H-phthalazin-1-ylacetic acid.]

EXAMPLE 1

In a double-blind clinical study with a parallel placebo group, 24 non-insulin dependent male diabetics were given either 50, 300 or 600 mg of ponalrestat or placebo, once daily for six days. A total of six subjects were tested at each regimen. The subjects were continued on their essential diabetic medication throughout the study and also received a weight-maintaining diabetic diet. Safety was determined by means of physical examinations, measurements of vital signs, interviews for subject symptomatology, electrocardiograms and routine clinical laboratory tests (including serum uric acid concentrations). The serum chemistries were done on fasting samples obtained prior to the first and fourth dose of study medication. Laboratory tests also were obtained on fasting serum samples taken at 24 and 48 hours after the sixth dose of study medication. The ponalrestat was tolerated well and there were no clinically significant drug-related abnormalities in clinical laboratory tests or electrocardiograms. However, a significant reduction in serum uric acid levels was observed as shown in FIG. 1 below:

Figure 1

Effects on serum uric acid levels of orally administered ponalrestat in male non-insulin dependent diabetics

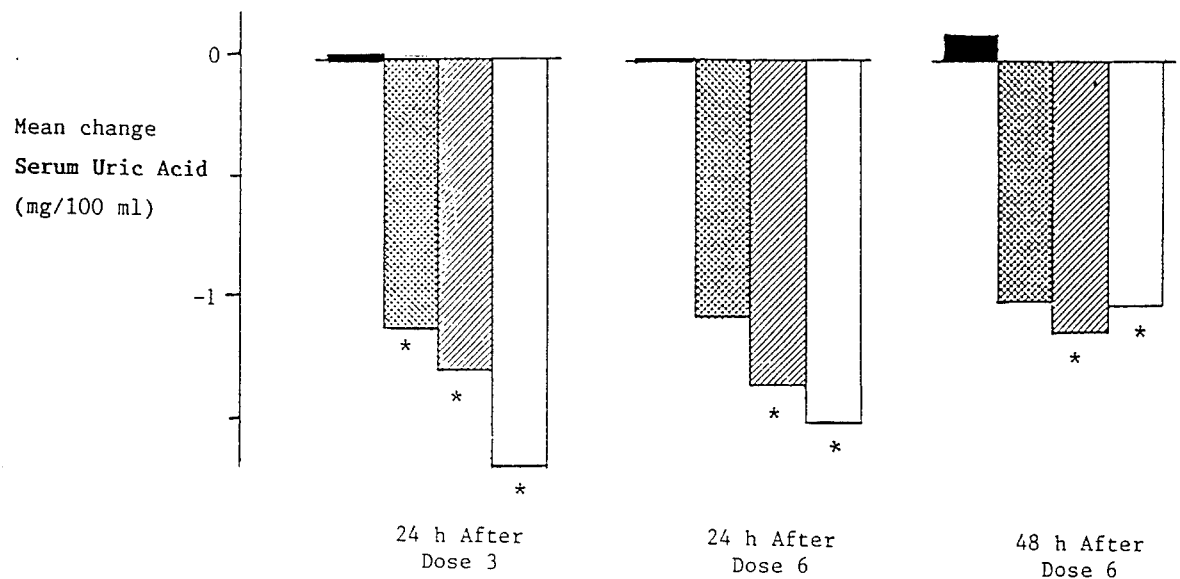

Means of individual changes from baseline in serum uric acid concentrations after 3 and 6 daily oral doses of ▰ placebo; and ponalrestat at ▒ 150 mg; ▨ 300mg; and ▢ 600 mg

* $p < 0.05$, n=6; except for placebo group 24 hr after dose 6 when n=5

EXAMPLE 2

In a double-blind study with a parallel placebo group, 24 non-pregnant, healthy, female subjects with intact ovarian function received either ponalrestat at 600 mg (12 subjects) or placebo (12 subjects) once daily for 27 days. The subjects were required not to consume alcoholic drinks or to eat cabbage, cauliflower, brussel sprouts, broccoli or smoked or charcoal-broiled meats, but were permitted to consume up to two cups per day of coffee, tea or other caffeinated drink. Safety was determined by means of physical examination, measurements or vital signs, interviews of subjective symptomatology, electrocardiograms and routine clinical laboratory tests (including serum uric acid concentrations). The serum chemistries were done on fasting samples obtained prior to the 1st, 7th, 14th and 21st dose of the study medication. Laboratory tests were also obtained on fasting serum samples obtained 24 hours after the twenty-seventh dose of study medication. The ponalrestat was well tolerated and there were no clinically significant drug-related abnormalities in clinical laboratory tests or electrocardiograms. However, ponalrestat caused a significant fall in serum uric acid levels and, in many subjects, to levels outside the normal range (approx. 2.5–7.5 mg/100 ml). Serum uric acid levels in the placebo group remained essentially unchanged throughoiut the study.

By way of comparison, the known hypouricaemic agent probenecid when dosed orally to eight normal subjects decreased the mean serum uric acid concentration from 5.5 mg/100 ml to 3.5 mg/100 ml 24 hours after drug (Vlasses et alia, Clin. *Pharmacol. Ther.*, 1981, 29, 798–807).

EXAMPLE 3

In a single-blind, multiple-dose investigation, comparisons were made of the effects of ponalrestat, placebo and probenecid on renal clearance of uric acid in normal male subjects. Using a randomised, parallel design, (1) six subjects received ponalrestat (600 mg p.o.) once daily for 3 days, (2) six subjects received an oral placebo dose once daily for 3 days, and (3) six subjects received probenecid (250 mg p.o.) every 12 hours for five doses. The subjects consumed a standardised diet for two days prior to the receipt of study medication and on each day of the study. Blood and urine samples were obtained periodically for the analysis of inter alia uric acid. The total urine output per subject was collected in 12 hour portions, stored under mineral oil and adjusted to pH>8 to ensure that all uric acid was in solution. Serum and urine uric acid levels were then determined by the uricase method. Mean serum uric acid concentrations were determined at the mid-point of each 12 hour urine collection. From these various determinations, it was found that ponalrestat produced a reduction in serum uric acid concentration similar to that of probenecid. Thus, by way of illustration:

| Agent | Day | 24 hr Urinary Uric Acid (mg) | Serum Uric Acid * (mg/100 ml) |
|---|---|---|---|
| Ponalrestat | 0 | 633 | 5.35 |
| Ponalrestat | 1 | 1191 | 3.95 |
| Probenecid | 0 | 586 | 4.35 |
| Probenecid | 1 | 1071 | 3.60 |
| Placebo | 0 | 654 | 4.92 |
| Placebo | 1 | 782 | 5.38 |

[* Serum uric acid levels: Day 0 figure is 18 hours prior to 1st dose Day 1 figure is 18 hours after 1st dose]

No toxic or other untoward signs were observed in the above study.

Formula I (ponalrestat) referred to herein:

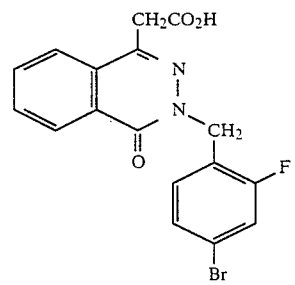

I claim:

1. A method for the production of a hypouricaemic effect in a warm blooded animal requiring such treatment which comprises administering to said animal a hypouricaemically effective amount of 3-(4-bromo-2-fluorobenzyl)-4-oxo-3H-phthalazin-1-ylacetic acid or of a pharmaceutically acceptable salt thereof.

2. A method as claimed in claim 1 wherein the pharmaceutically acceptable salt of the acid is selected from alkali metal and alkaline earth metal salts, aluminium and ammonium salts, and salts with organic bases affording a pharmaceutically acceptable cation such as salts with triethanolamine.

3. A method as claimed in claim 2 wherein the pharmaceutically acceptable salt of the acid is a sodium or potassium salt.

* * * * *